US00PP35347P2

(12) United States Plant Patent
Clark

(10) Patent No.: US PP35,347 P2
(45) Date of Patent: Aug. 22, 2023

(54) ***COLEUS* PLANT NAMED 'UF20-73-3'**

(50) Latin Name: *Coleus scutellarioides*
Varietal Denomination: UF20-73-3

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/803,905

(22) Filed: Jan. 13, 2023

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469
See application file for complete search history.

(56) References Cited

U.S. PATENT DOCUMENTS

PP32,980 P3 4/2021 Clark

*Primary Examiner* — Susan McCormick Ewoldt
(74) *Attorney, Agent, or Firm* — Koenig IP Works, PLLC; Katherine Koenig

(57) ABSTRACT

A new and distinct cultivar of *Coleus* (*Coleus scutellarioides*) plant named 'UF20-73-3', selected for having a combination of desirable traits that make it well-suited for good performance as an annual plant in the summer landscape. 'UF20-73-3' was selected for its consistent foliage color patterning and for its fast growth rate and vigor in the greenhouse and landscape. 'UF20-73-3' has foliage that is predominantly deep purple with consistent deep pink centers, and well-defined bright lime green accents at the leaf margin. 'UF20-73-3' is exceptional because it maintains a strong pink center and bright leaf margins in a broad range of environmental conditions. It is a vigorous plant that can easily grow to four feet tall in the landscape in one season, maintaining similar color in both sun and shade. It is upright, spreading, highly branched and grows wider than it does tall.

5 Drawing Sheets

Genus and species: *Coleus scutellarioides*.
Cultivar denomination: 'UF20-73-3'.

CROSS-REFERENCE TO RELATED APPLCIATIONS

N/A.

ACKNOWLEDGEMENT OF FEDERAL RESEARCH SUPPORT

N/A.

BACKGROUND OF THE NEW CULTIVAR

The invention relates to a new and distinct cultivar of *Coleus* plant named 'UF20-73-3'. The new cultivar 'UF20-73-3' originated from an open pollination conducted in May-November 2017 in Citra, Fla., between the female *Coleus* plant 'UF19-86-1' (unpatented) and an unknown male *Coleus* plant. A single seedling was chosen in May 2020 for further asexual propagation in Gainesville, Fla.

The new cultivar 'UF20-73-3' has been reproduced asexually for over 18 months through vegetative meristem tip cuttings and has been found to retain its distinctive characteristics through successive asexual propagations. 'UF20-73-3' was first propagated asexually by vegetative meristem tip cuttings in May 2020 in Gainesville, Fla., and has remained true-to-type since that time.

Plant Breeder's Rights for the new cultivar 'UF20-73-3' have not been applied for, and 'UF20-73-3' has not been made publicly available more than one year prior to the filing date of this application.

When compared to the female parent 'UF19-86-1', the new cultivar 'UF20-73-3' has larger leaves that are longer than they are wide. Leaves of 'UF20-73-3' are colored predominantly deep purple with bright lime green margins, prominent deep pink centers and mid-veins and cream-colored leaf bases. In contrast, 'UF19-86-1' has smaller leaves that are equally as long as they are wide and are colored dark maroon with dark green margins and only small traces of pink color on older leaves. 'UF20-73-3' has a vigorous, upright and spreading habit with more lateral branching, whereas 'UF19-86-1' is less vigorous, and more upright in habit with less lateral branching.

The new cultivar 'UF20-73-3' was selected for its consistent foliage color patterning, and for its fast growth rate and vigor in the greenhouse and landscape. 'UF20-73-3' has foliage that is predominantly colored deep purple with consistent pink centers, and well-defined lime green leaf margins. Normally this color combination fades in either full sun (predominantly maroon-brown) or full shade (predominantly green), with the consistent loss of pink color. 'UF20-73-3' is exceptional because it maintains a strong pink center and bright colored leaf margin in a broad range of environmental conditions. It is a vigorous cultivar that can easily grow to four feet tall in the landscape, maintaining similar color in both sun and shade. Vegetative cuttings of 'UF20-73-3' form roots in one week and consistently produce vivid pink colored foliage in the greenhouse.

SUMMARY OF THE INVENTION

The new cultivar 'UF20-73-3' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF20-73-3' when grown under normal horticultural practices in Gainesville, Fla.: 'UF20-73-3' has the combination of vigorous, upright and spreading growth habit, excellent heat tolerance, and consistent multicolored leaves that are significantly different than other *Coleus* plants; it has superior stability in foliage color in both sun and shade conditions, maintaining stable color in all conditions; it has excellent lateral branching, making it suitable for propagators and producers; and 'UF20-73-3' has been observed to have long-season performance in landscape trials in Gainesville, Fla.

DESCRIPTION OF THE FIGURES

This new *Coleus* cultivar 'UF20-73-3' is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar;

FIG. 3 shows a close-up view of the foliage of the new *Coleus* cultivar;

FIG. 4 shows the adaxial side of an immature leaf (left) and a mature leaf (right) of the new *Coleus* cultivar with corresponding R.H.S. color designations; and FIG. 5 shows the abaxial side of an immature leaf (left) and a mature leaf (right) of the new *Coleus* cultivar with corresponding R.H.S. color designations.

DETAILED BOTANICAL DESCRIPTION OF THE CULTIVAR

Figure 1:
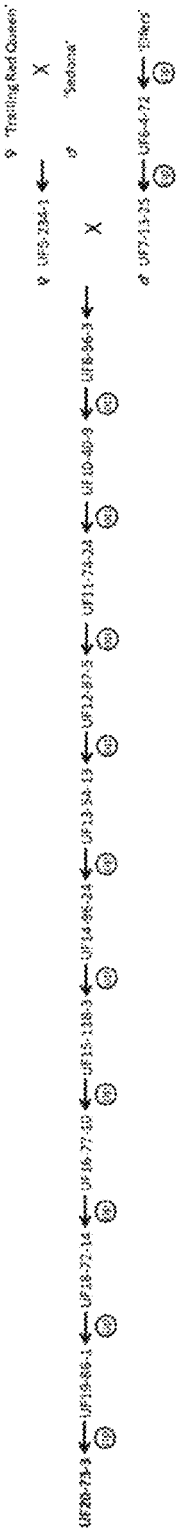
FIG. 1 shows the pedigree of the new *Coleus* cultivar 'UF20-73-3' shown and described herein.
Figure 2:
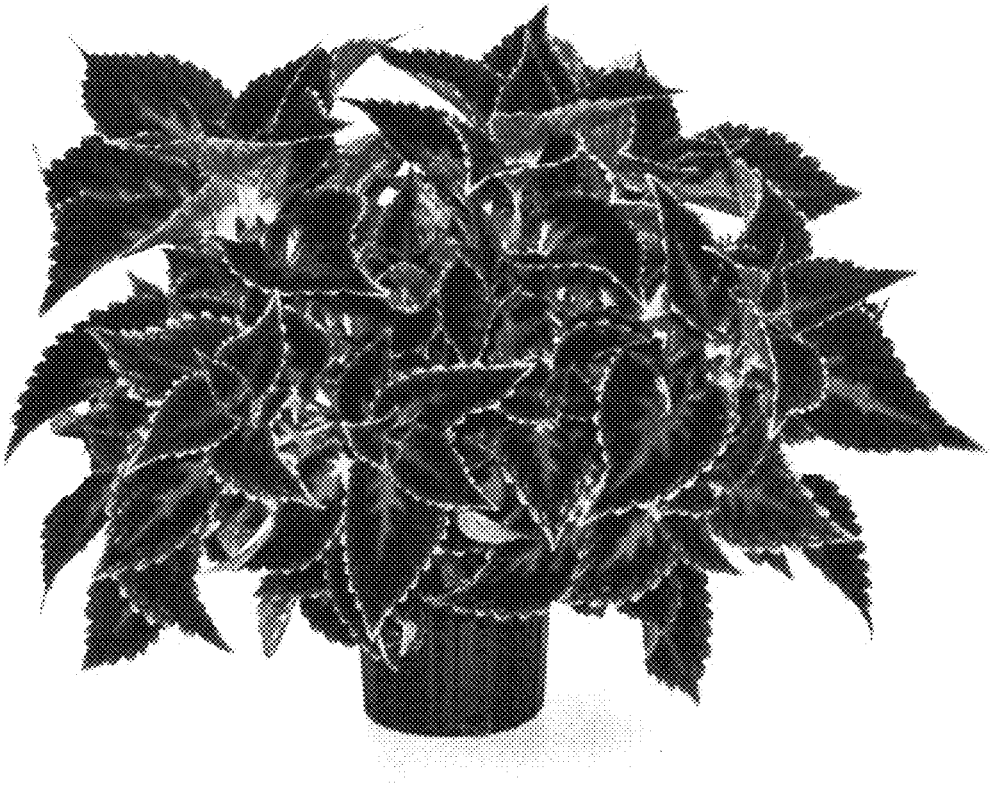
FIGS. 2-5 were taken from plants grown ten weeks from unrooted cuttings in February-April 2022 in a glass-covered greenhouse in Gainesville, Fla.
Figure 3:
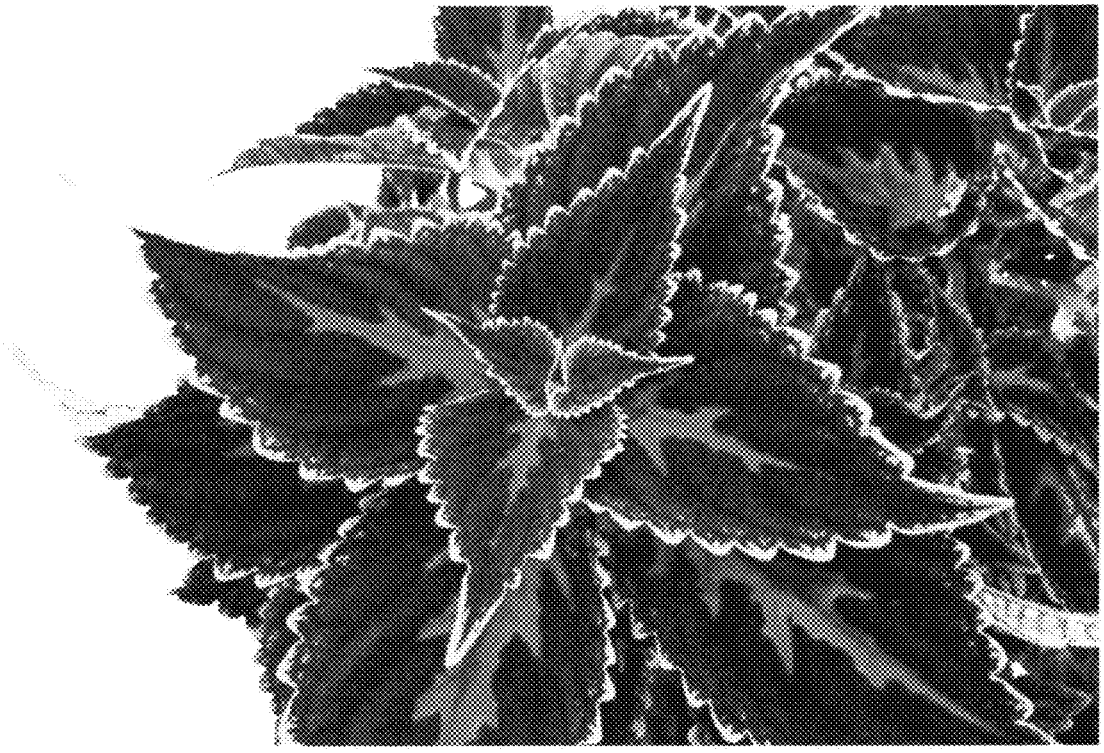
Figure 4:
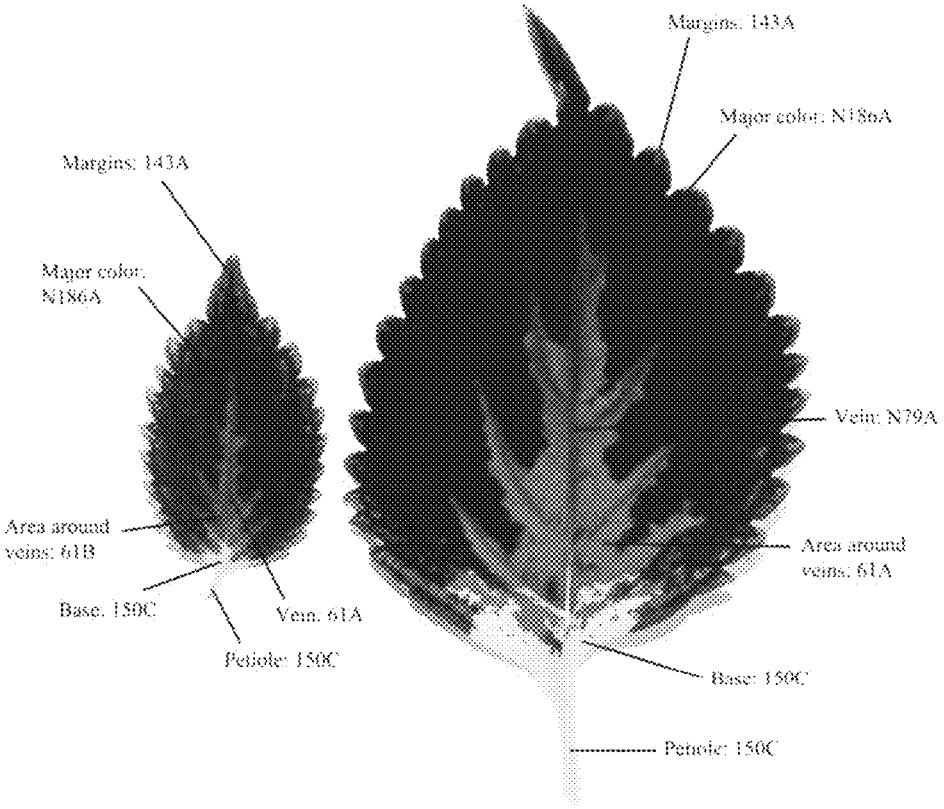
Figure 5:
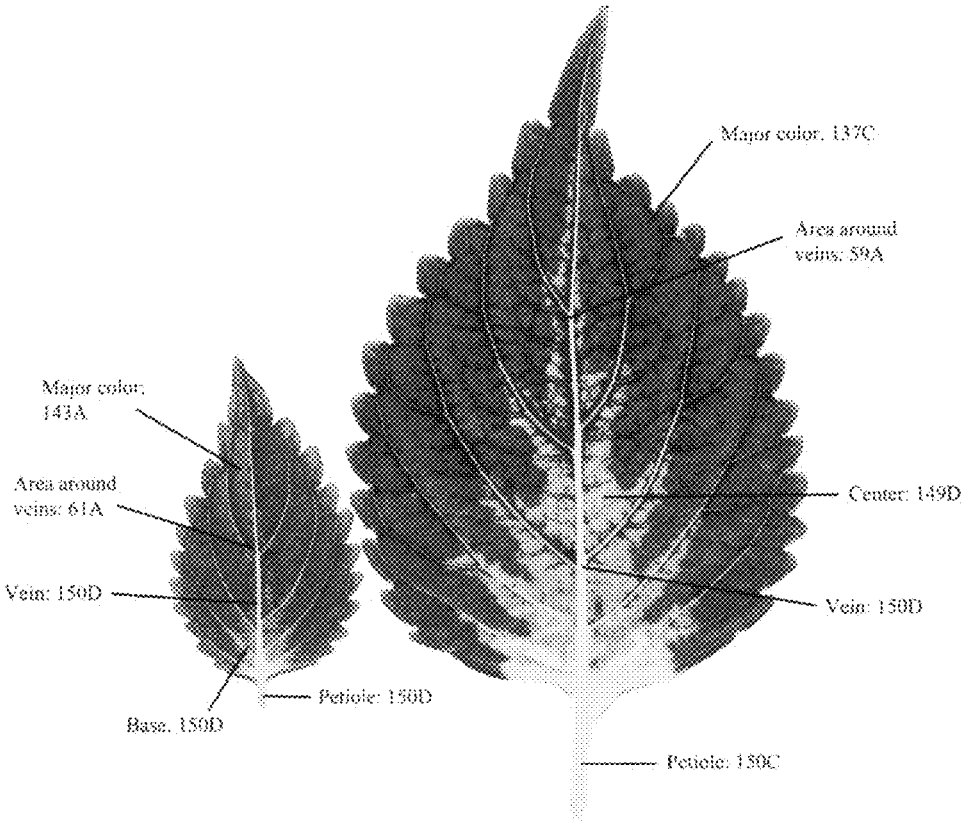

Foliage color was determined under full sun conditions in the middle of the day in a glass-covered greenhouse. Color references are to The R.H.S. Colour Chart of The Royal Horticultural Society of London (R.H.S.), 2007 5th Edition. *Coleus* leaves are rarely one solid color but encompass hues, shades and tints, and color patterns differ from one genotype to another due to varying levels of variegation. The following detailed description of 'UF20-73-3' was obtained using ten-week-old plants grown from unrooted cuttings in February-April 2022 in a glass-covered greenhouse in Gainesville, Fla. The plants were propagated in mist for ten days after cuttings were stuck, then grown in one-gallon pots for approximately eight and a half additional weeks.

Botanical Description

Botanical classification:
- *Family*.—Lamiaceae.
- *Botanical name*.—*Coleus scutellarioides*.
- *Common name*.—*Coleus*.
- *Cultivar*.—'UF20-73-3'.

Parentage:
- *Female or seed parent*.—'UF19-86-1'.
- *Male or pollen parent*.—Unknown.

Propagation:
- *Type cuttings*.—Vegetative meristem tip cuttings having at least 1 node.
- *Time to initiate roots*.—3-4 days.
- *Time to produce a rooted cutting*.—7-10 days.
- *Root habit*.—Fibrous.
- *Root description*.—Callus forms in 2-3 days, roots initiate in 3-4 days and become a highly branched cutting in 7-10 days.

Plant description:
- *Habit*.—Upright and spreading.
- *Height* (*from top of soil*).—30-35 cm.
- *Width* (*horizontal plant diameter*).—70-75 cm.

Branches:
- *Quantity per plant*.—Approximately 15.
- *Branch color*.—RHS 134A (yellowish green).
- *Texture*.—Smooth.
- *Pubescence*.—Not present.
- *Stem description*.—Square-shaped stem.
- *Branch diameter*.—0.8-0.9 cm at the base of a 28-cm-long branch.
- *Branch length*.—3.5-4.0 cm measured at mid-branch.
- *Internode length*.—3.5-4.0 cm measured at mid-branch.
- *Anthocyanin*.—Not present.

Leaves:
- *Quantity of leaves per branch*.—20-22.
- *Arrangement*.—Opposite.
- *Fragrance*.—Not fragrant.
- *Shape*.—Ovate.
- *Length*.—16-17 cm.
- *Width*.—10-11 cm.
- *Apex*.—Broadly acute.
- *Base*.—Attenuate.
- *Margin*.—Crenate.
- *Leaf texture*.—Upper surface: Pulverulent. Lower surface: Smooth.
- *Venation color, mature leaf*.—Upper surface, major color: RHS N79A (purplish red). Upper surface, base: RHS 150C (yellow green). Lower surface: RHS 150D (yellow green).
- *Venation color, immature leaf*.—Upper surface: RHS 61A (purplish red). Lower surface: RHS 150D (yellow green).
- *Venation pattern*.—Upper surface: Reticulate. Lower surface: Reticulate.
- *Color, immature leaf*.—Upper surface, major color: RHS N186A (purplish grey). Upper surface, edges: RHS 143A (yellow green). Upper surface, center: RHS 61B (purplish red). Upper surface, base: RHS 150C (yellow green). Lower surface, major color: RHS 143A (yellow green). Lower surface, spots around veins: RHS 61A (purplish red). Lower surface, base: RHS 150D (yellow green).
- *Color, mature leaf*.—Upper surface, major color: RHS N186A (purplish grey). Upper surface, edges: RHS 143A (yellow green). Upper surface, center: RHS 61A (purplish red). Upper surface, base: RHS 150C (yellow green). Lower surface, major color: RHS 137C (yellow green). Lower surface, color around veins: RHS 59A (dark red). Lower surface, center: RHS 149D (yellow green).
- *Petiole length*.—3.5-4.0 cm.
- *Petiole diameter*.—0.3-0.4 cm.
- *Petiole color, mature leaf* (*both upper and lower surfaces*).—RHS 150C (yellow green).

*Petiole color, immature leaf.*—Upper surface: RHS 150C (yellow green). Lower surface: RHS 150D (yellow green).

*Petiole texture.*—Smooth, no pubescence.

Flowers and seeds: Flowers and seeds have not been observed to date during formal trials in Gainesville, Fla.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* spp.), which occur on older stock plant material held in the greenhouse for over 3-4 months. *Impatiens* Necrotic Spot Virus (Bunyaviridae) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

Comparison with Known Cultivars

When the new cultivar 'UF20-73-3' is compared to the commercial cultivar 'UF17-50-5' (U.S. Plant Pat. No. 32,980, commercial name "Mainstreet Alligator Alley"), 'UF20-73-3' has leaves with a predominately colored deep purple with consistent pink centers, and well-defined lime green coloration along the leaf margins, whereas 'UF17-50-5' has a narrower purplish red center coloration and a broader yellow green coloration along the leaf margins.

What is claimed is:

1. A new and distinct *Coleus scutellarioides* plant named 'UF20-73-3' as shown and described herein.

* * * * *